(12) United States Patent
Wu et al.

(10) Patent No.: US 9,005,309 B2
(45) Date of Patent: Apr. 14, 2015

(54) FOUR-LINK HYDRAULIC BUFFER KNEE JOINT ASSEMBLY

(75) Inventors: Fu-Kuo Wu, New Taipei (TW); Hsiang-Ming Wu, New Taipei (TW)

(73) Assignee: Ken Dall Enterprise Co., Ltd., New Taipei (TW)

( * ) Notice: Subject to any disclaimer, the term of this patent is extended or adjusted under 35 U.S.C. 154(b) by 338 days.

(21) Appl. No.: 13/612,875

(22) Filed: Sep. 13, 2012

(65) Prior Publication Data

US 2013/0085580 A1 Apr. 4, 2013

(30) Foreign Application Priority Data

Sep. 30, 2011 (TW) .............................. 100135412 A

(51) Int. Cl.
| | |
|---|---|
| *A61F 2/62* | (2006.01) |
| *A61F 2/64* | (2006.01) |
| *A61F 2/68* | (2006.01) |
| A61F 2/50 | (2006.01) |
| A61F 2/74 | (2006.01) |

(52) U.S. Cl.
CPC . *A61F 2/644* (2013.01); *A61F 2/68* (2013.01); *A61F 2002/5006* (2013.01); *A61F 2002/503* (2013.01); *A61F 2002/5033* (2013.01); *A61F 2002/5075* (2013.01); *A61F 2002/5086* (2013.01); *A61F 2002/6818* (2013.01); *A61F 2002/745* (2013.01)

(58) Field of Classification Search
CPC ....................................................... A61F 2/644
USPC ............................................................ 623/39
See application file for complete search history.

*Primary Examiner* — Jacqueline Woznicki
(74) *Attorney, Agent, or Firm* — Leong C. Lei

(57) ABSTRACT

A four-link hydraulic buffer knee joint assembly which includes a hydraulic center axle configured at a center hole of a four-link hydraulic main body and utilizes a spring force and an oil-filling piston to achieve the auto-filling of hydraulic oil. The hydraulic center axle is able to utilize adjustable knobs provided on an outer side of the center axle to adjust the bending speed and the spring-back recovery speed. The setting location of the hydraulic center axle differs from the one of conventional joint assembly such that the overall size of the knee joint assembly is reduced while the joint assembly includes the functions of adjustable hydraulic bending and stretching speeds and buffering for the hydraulic head to return to its horizontal state. The four-link hydraulic main body comprises a setting changeable controlling axle for achieving the function of the buffered safety brake against the ground.

5 Claims, 19 Drawing Sheets

FOUR-LINK HYDRAULIC BUFFER KNEE JOINT ASSEMBLY

TECHNICAL FIELD OF THE INVENTION

The present invention is related to a four-link hydraulic buffer knee joint assembly, in particular, to a knee joint assembly utilizing the change setting of the hydraulic center axle as well as the safety device to adjust the buffering speed and the buffered safety brake thereof.

DESCRIPTION OF THE PRIOR ART

Conventional artificial knee joints mostly adapt the design of a complex linkage assembly in order to achieve the simulated knee joint bending effects. As the knee joint is extended to reach the ground and is subject to an impact force, the connecting rod actuated is able to press against a cushion such that the impact force can be absorbed along the direction of the leg. Nevertheless, since the walking speeds or paces of the users requiring the aid of artificial knee joints vary from one another, the shock absorbing effects produced by such conventional artificial knee joints also vary greatly and their conformabilities to users differ from one another in addition to the fact that the overall lengths of such conventional knee joints are greater due to their design of complex linkage assembly.

As the medical development improves and the technology in the medical field advances over time, artificial knee joints are now equipped with the designs of pneumatic and hydraulic buffer mechanisms and are capable of generating better buffering effects or shock absorptions; however, the overall length of an artificial knee joint is yet to be improved such that it can be easily adapted to persons of different heights and without imposing limitations to the user's height.

SUMMARY OF THE INVENTION

The present invention is related to a four-link hydraulic buffer joint assembly comprising a four-link hydraulic head, a motion linkage device, a spring device, a buffering device and a cushion member assembled with axles respectively. Said four-link hydraulic head is configured to be attached upward to a thigh and a lower end of said cushion member is configured to be attached downward to a calf; wherein: a connecting rod is attached to an inner groove of said four-link hydraulic head; a plurality of perforations provided on an outer side of said four-link hydraulic head are connected with arched slats and pulling rods and are secured thereon by attaching needle bearings and flat-head inner hexagon screws as well as center axles thereto; a through-hole provided at a lower end of said connecting rod is aligned with said groove of said four-link hydraulic head and is secured thereon by attaching needle bearings and center axles thereto; a through-hole provided at a lower end of said pulling rod is aligned with a central hole of a four-link hydraulic main body and is secured thereon via flat-head inner hexagon screws fastened thereto; a through-hole provided at a lower end of said four-link hydraulic main body is engaged with a through-hole of said cushion member and is secured thereon by attaching a needle bearing with a center axle thereto; an outer side of said through-hole of said cushion member is engaged with arched slats secured thereon via a plurality of flat-head inner hexagon screws fastened thereto; an inner groove of said connecting rod is engaged with a through-hole provided on an upper end of said spring device and is secured thereon by attaching needle bearings and washers with center axles thereto; a lower end of said spring device is engaged with a through-hole of a protrusion extending outward from said four-link hydraulic main body and is secured thereon by attaching center axles, washers and needle bearings thereto; a lower end of said four-link hydraulic head is engaged with a shock absorber attached to a cushion wing.

The four-link hydraulic main body of the four-link hydraulic buffer knee joint assembly provided at an internal of said buffering device can be of a changed setting to comprise a controlling axle; and wherein said controlling axle comprises a fixation screw penetrating a star-shaped ring, a washer, a locking ring and a spring. Furthermore, an oil-filling control mechanism comprises an oil-filling piston and a plurality of rolling balls arranged therein.

In view of the abovementioned drawbacks that due to the variations in the walking speeds or paces of the users requiring the aid of artificial knee joints, the shock absorbing effects produced by conventional artificial knee joints also vary greatly and their conformabilities to users differ from one another in addition to the fact that the overall lengths of such conventional knee joints adapted the design of complex linkage assembly are great and are inconvenient to users, the inventor seeks to provide an improved hydraulic buffer joint assembly with an improved arrangement of a hydraulic center axle to reduce the overall size of the joint assembly to overcome the limitation on the height of user while providing the improved joint assembly with adjustable bending speed and spring-back recovery speed such that the hydraulic joint assembly can be worn or used by users with greater conform and safety. Also, the hydraulic center axle of the joint assembly is also equipped with an auto-oil-cycling hydraulic mechanism such that the overall use and the time of usage can be enhanced. In addition, the buffering device further comprises a safety device configured therein such that when it is tilted, it is able to block the oil passage in order to achieve the effect of adjusting the buffering speed of the joint assembly and providing a buffered safety brake against the ground.

DETAILED DESCRIPTION OF THE PREFERRED EMBODIMENTS

Figure 1:
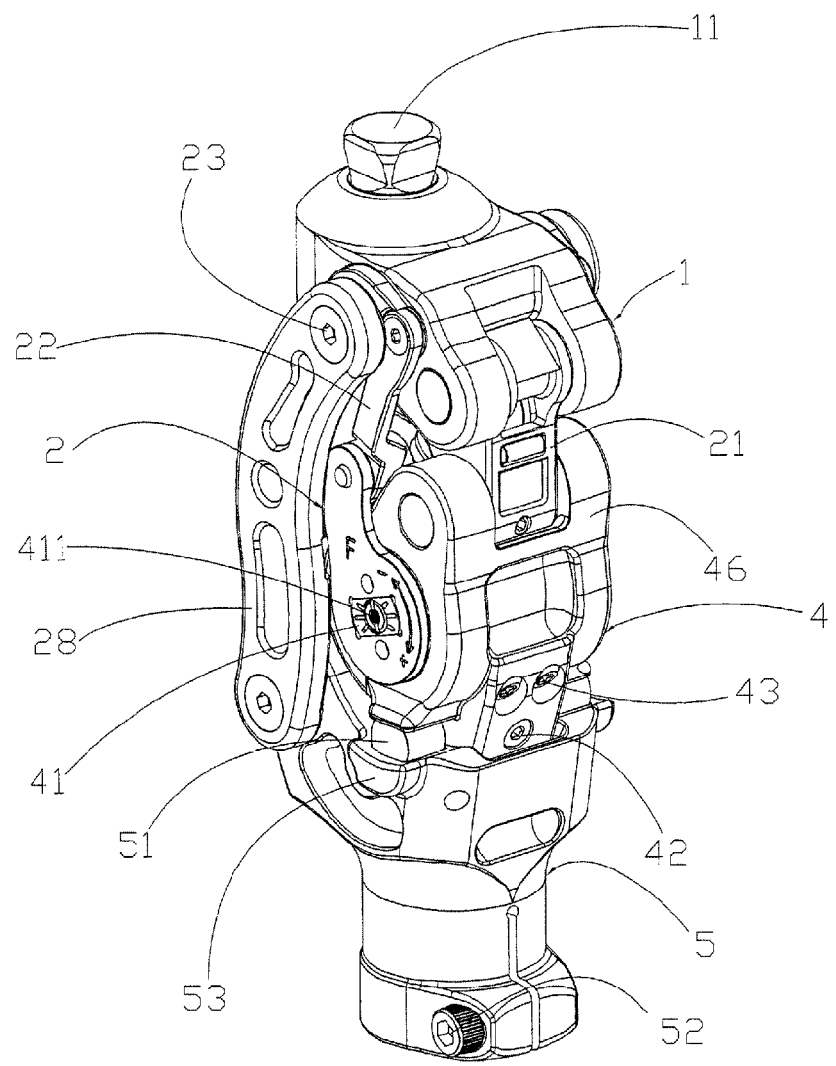
FIG. 1 is a perspective view of the hydraulic buffer joint assembly of the present invention.
Figure 2:
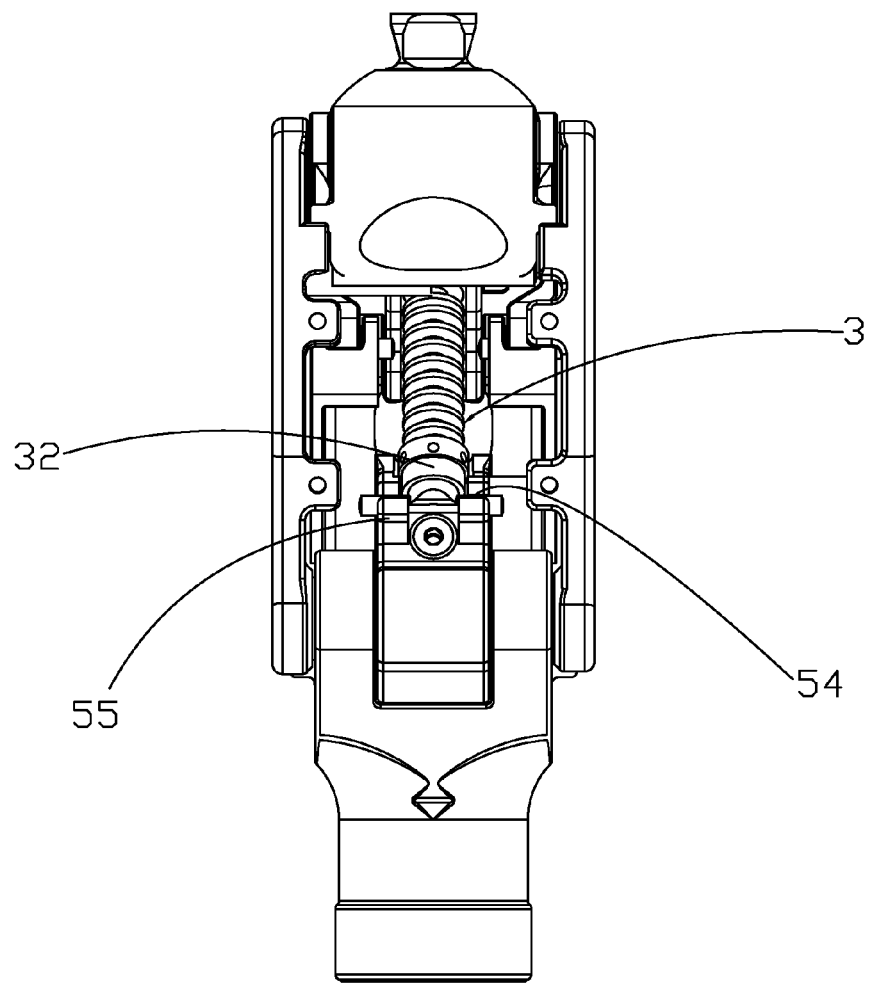
FIG. 2 is an illustration showing the hydraulic buffer joint assembly of the present invention.
Figure 3:
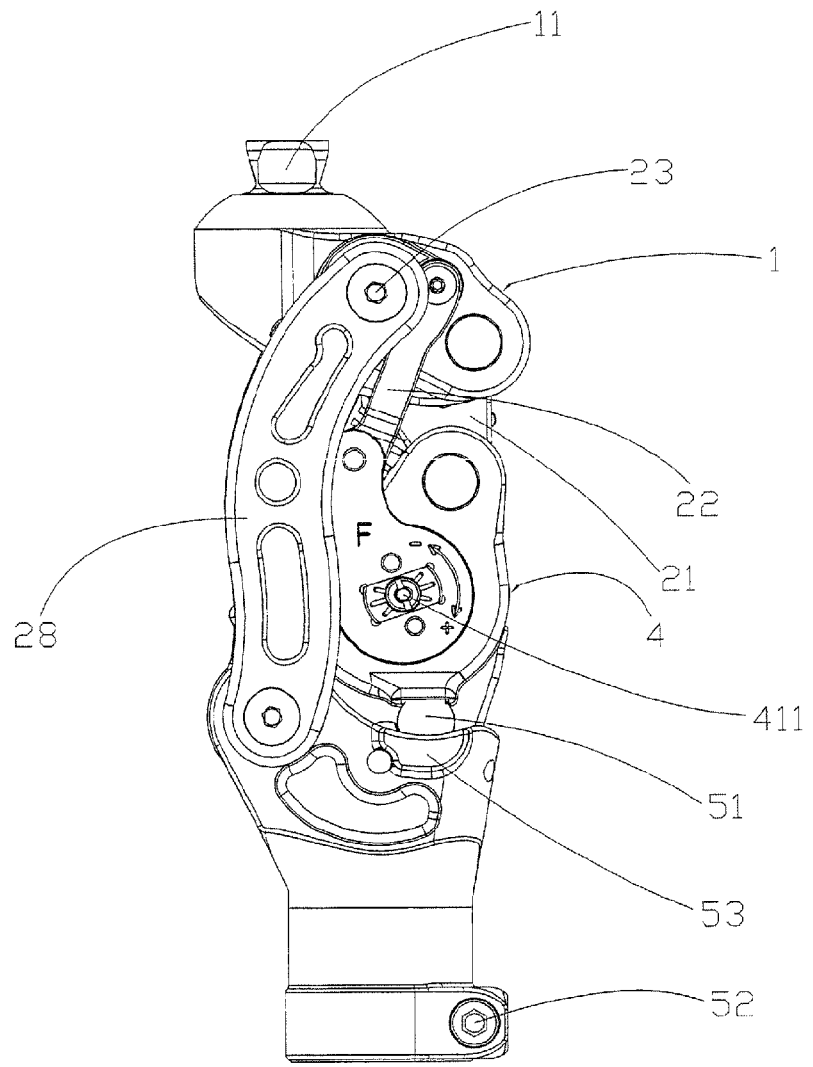
FIG. 3 is another illustration showing the hydraulic buffer joint assembly of the present invention.
Figure 4:
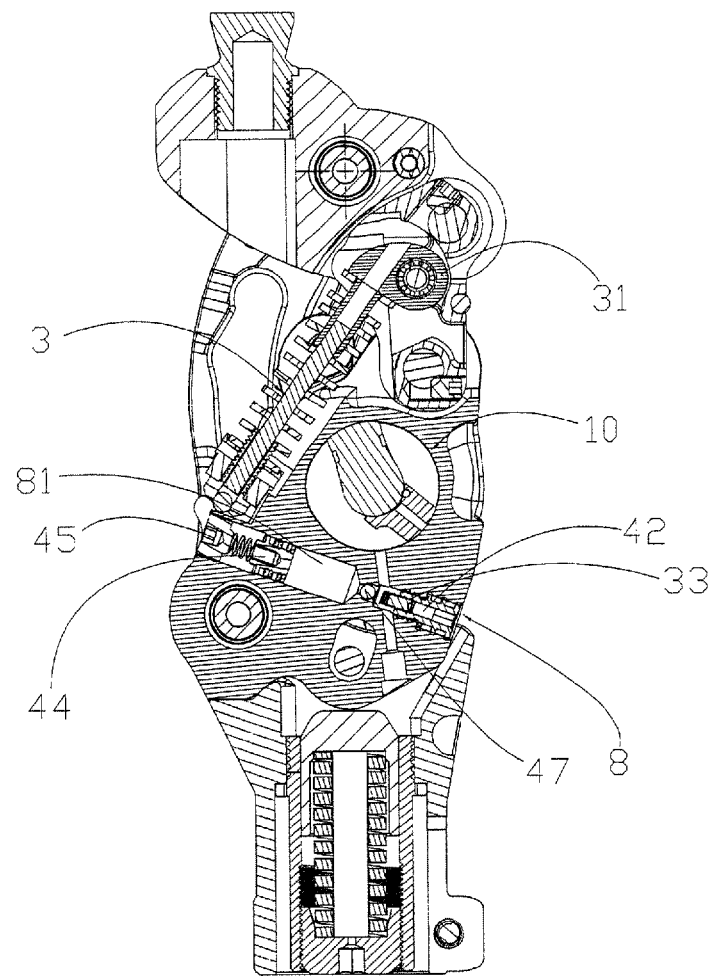
FIG. 4 is a cross sectional view of the hydraulic buffer joint assembly of the present invention.
Figure 5:
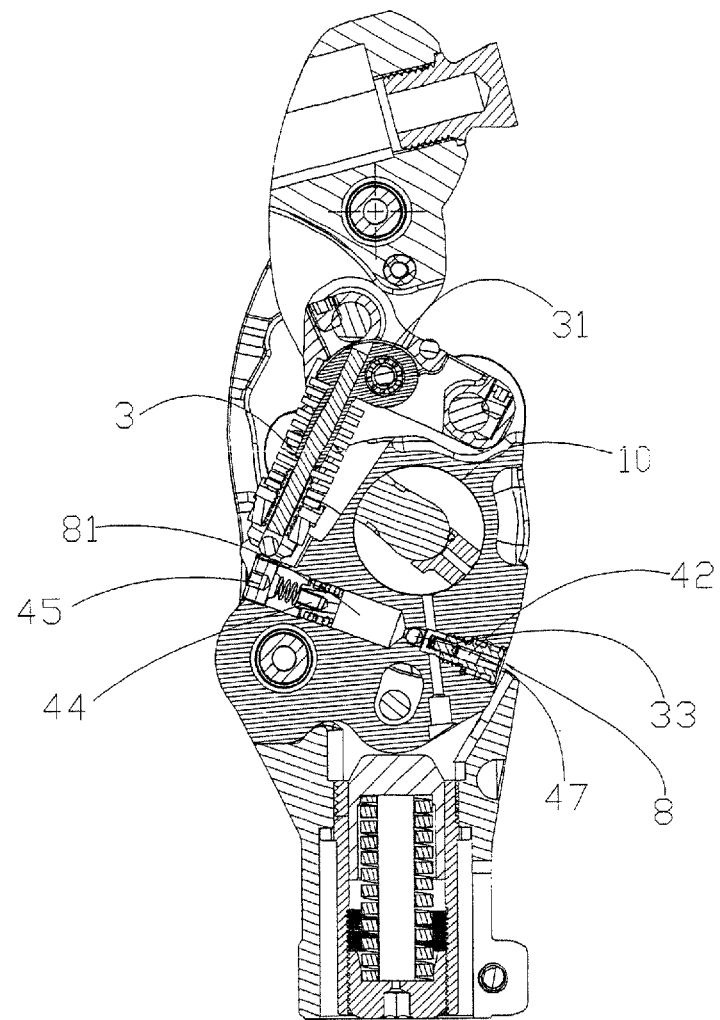
FIG. 5 is a cross sectional view of the hydraulic buffer joint assembly of the present invention.
Figure 6:
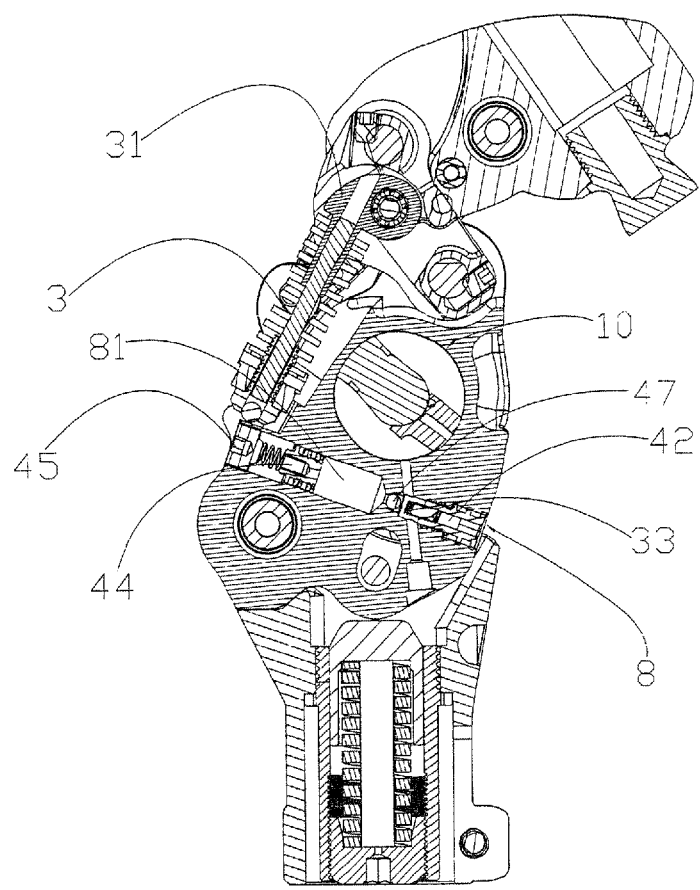
FIG. 6 is a cross sectional view of the hydraulic buffer joint assembly of the present invention.
Figure 7:
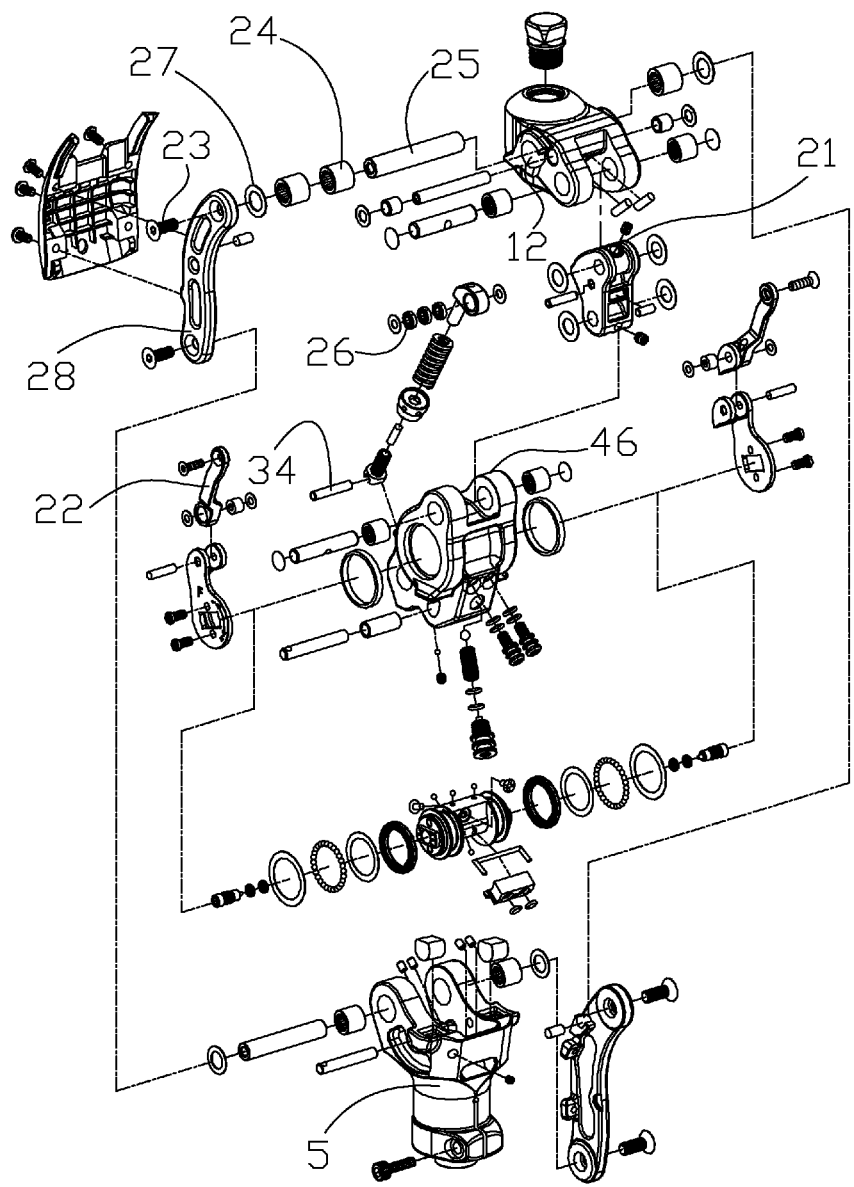
FIG. 7 is an exploded perspective view of the hydraulic buffer joint assembly of the present invention.
Figure 8:
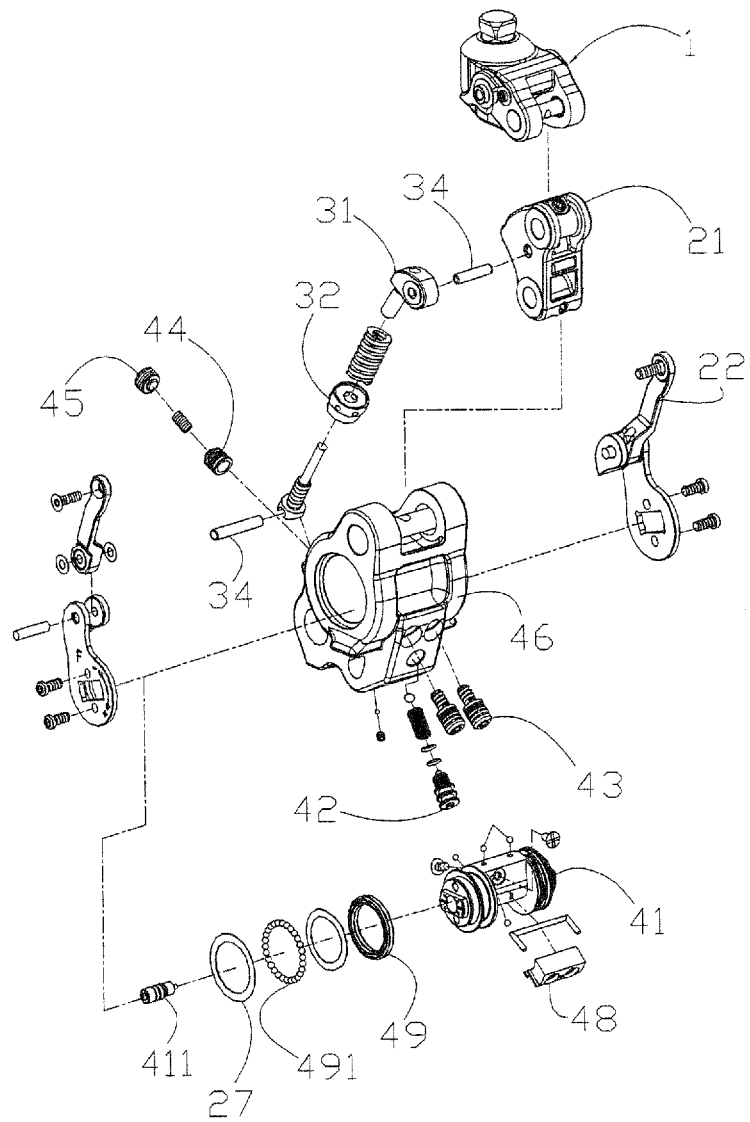
FIG. 8 is another exploded perspective view of the hydraulic buffer joint assembly of the present invention.
Figure 9:
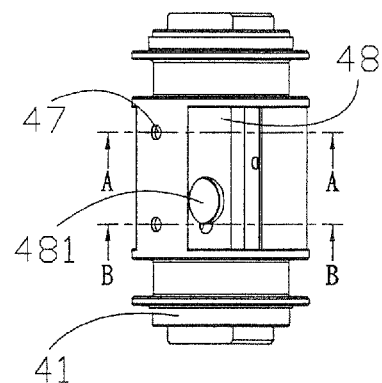
FIG. 9 is a cross sectional view of the hydraulic buffer joint assembly of the present invention.
Figure 9A:
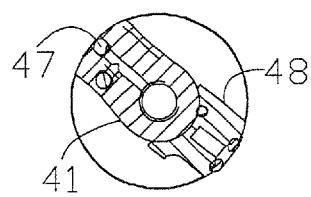
FIG. 9A is another cross sectional view of the hydraulic buffer joint assembly of the present invention taken along A-A line.
Figure 9B:
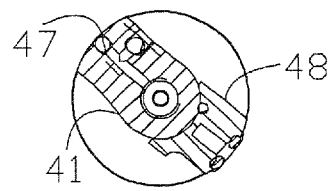
FIG. 9B is another cross sectional view of the hydraulic buffer joint assembly of the present invention taken along B-B line.
Figure 10:
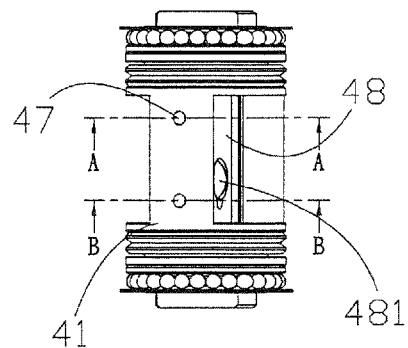
FIG. 10 is a cross sectional view of the hydraulic buffer joint assembly of the present invention.
Figure 10A:
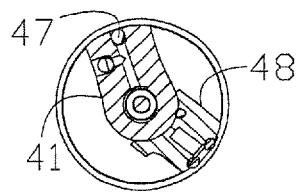
FIG. 10A is another cross sectional view of the hydraulic buffer joint assembly of the present invention taken along A-A line.
Figure 10B:
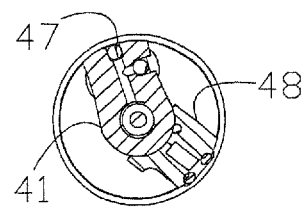
FIG. 10B is another cross sectional view of the hydraulic buffer joint assembly of the present invention taken along B-B line.
Figure 11:
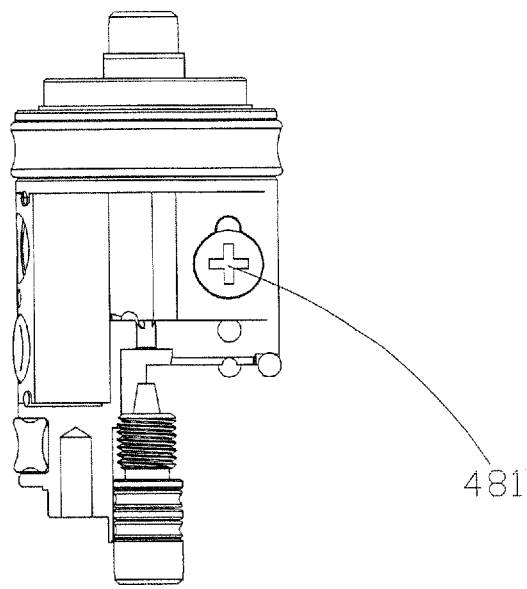
FIG. 11 is a cross sectional view of the hydraulic buffer joint assembly of the present invention.
Figure 11A:
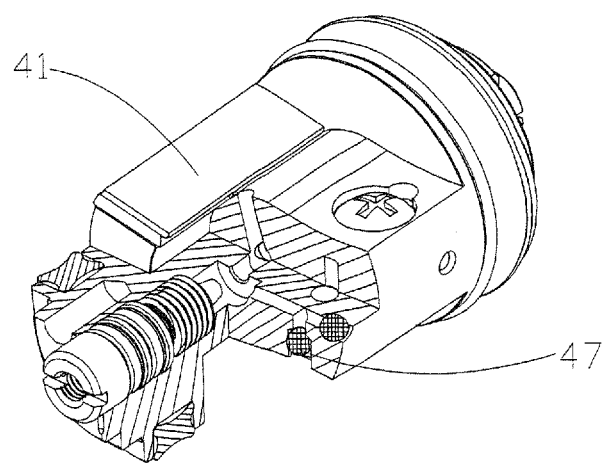
FIG. 11A is another cross sectional view at another viewing angle of the hydraulic buffer joint assembly of the present invention.
Figure 12:
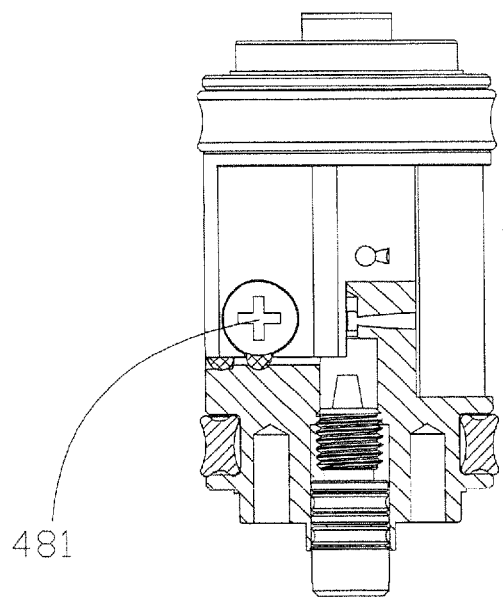
FIG. 12 is a cross sectional view of the hydraulic buffer joint assembly of the present invention.
Figure 12A:
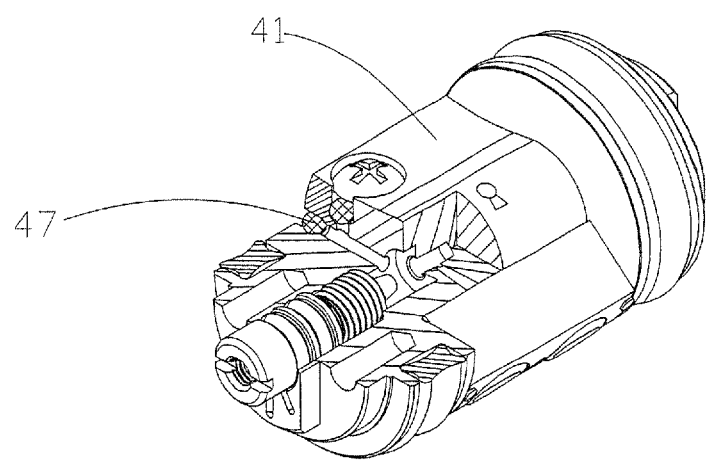
FIG. 12A is another cross sectional view at another viewing angle of the hydraulic buffer joint assembly of the present invention.
Figure 13:
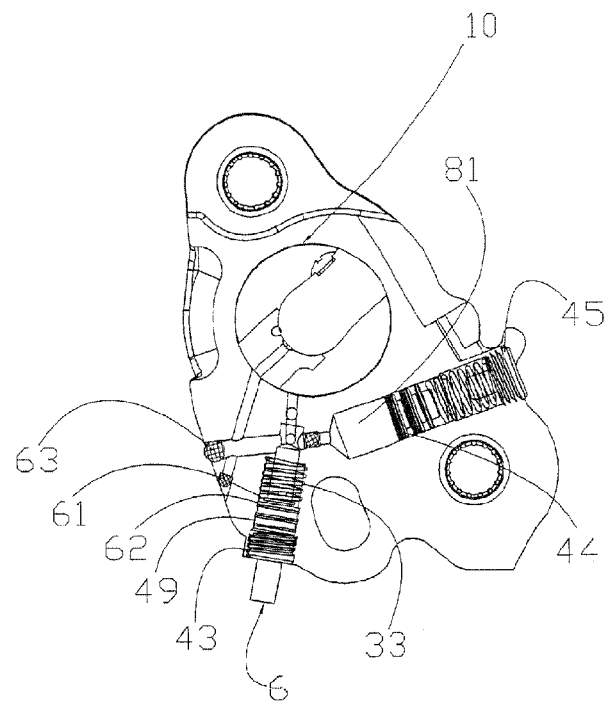
FIG. 13 is an illustration showing the hydraulic buffer joint assembly of the present invention.
Figure 13A:
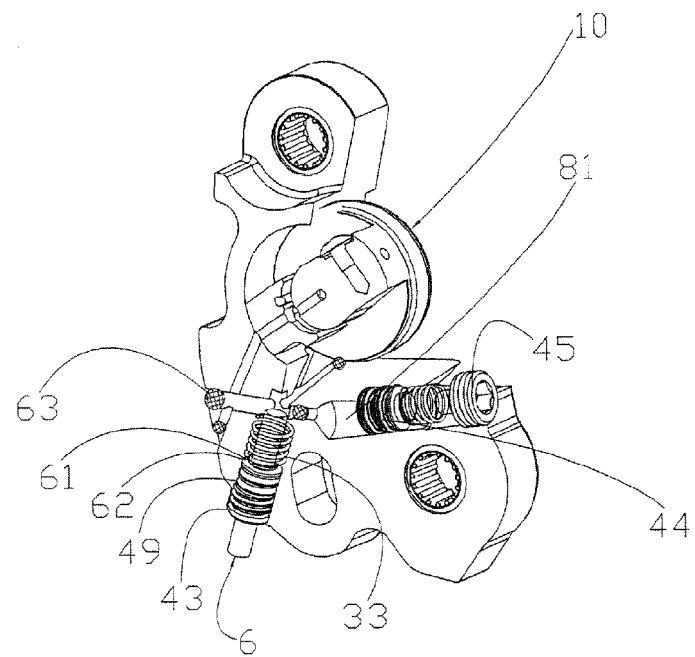
FIG. 13A is another illustration showing the hydraulic buffer joint assembly of the present invention.
Figure 14:
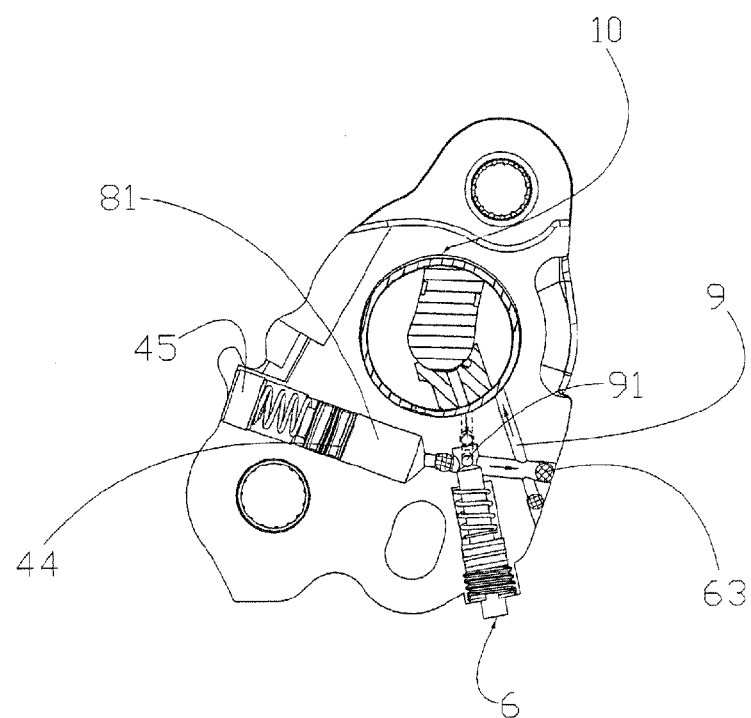
FIG. 14 is an illustration showing the hydraulic buffer joint assembly of the present invention.
Figure 15:
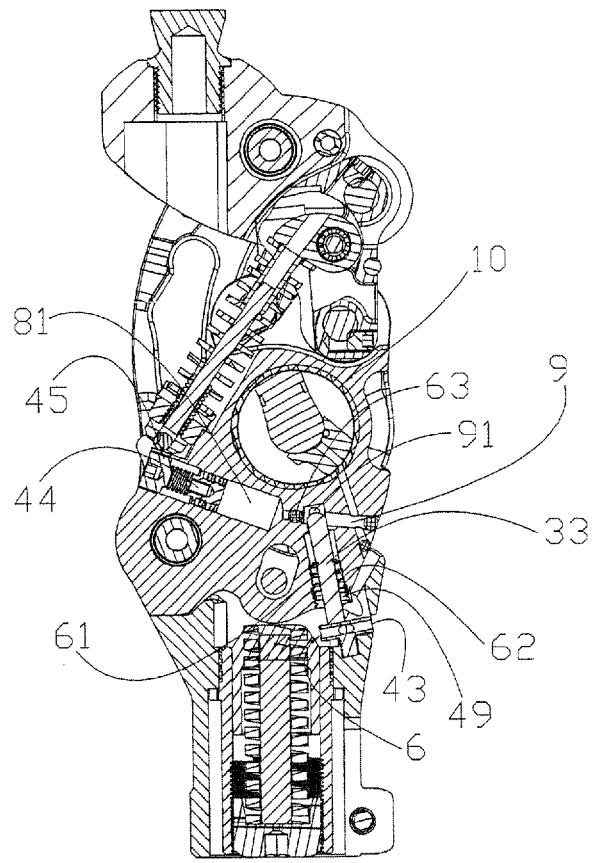
FIG. 15 is a cross sectional view of the hydraulic buffer joint assembly of the present invention.
Figure 16:
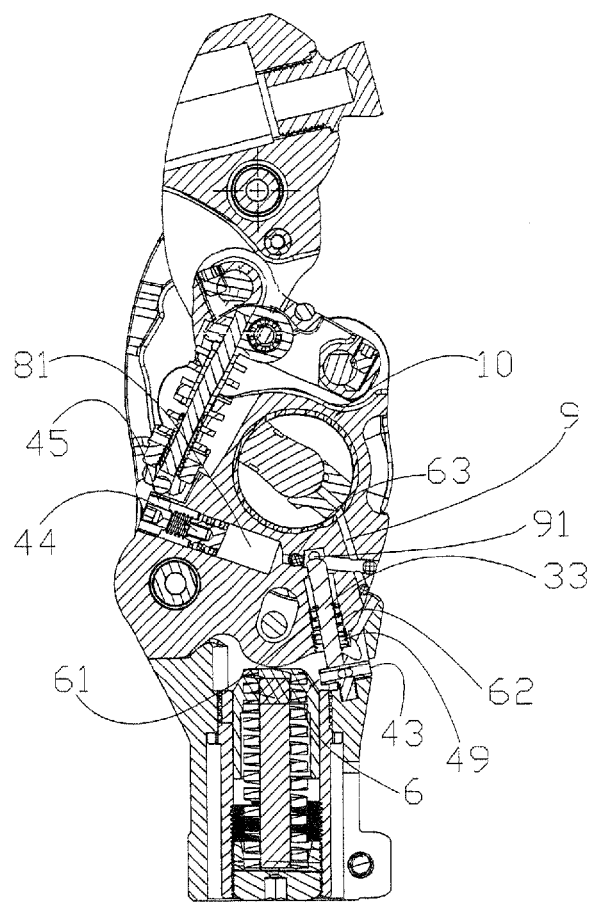
FIG. 16 is a cross sectional view of the hydraulic buffer joint assembly of the present invention.
Figure 17:
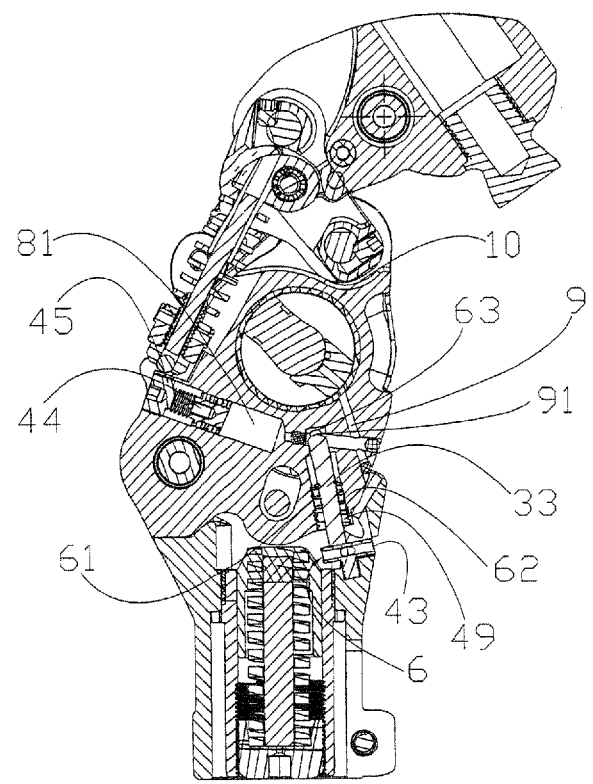
FIG. 17 is a cross sectional view of the hydraulic buffer joint assembly of the present invention.
Figure 18:
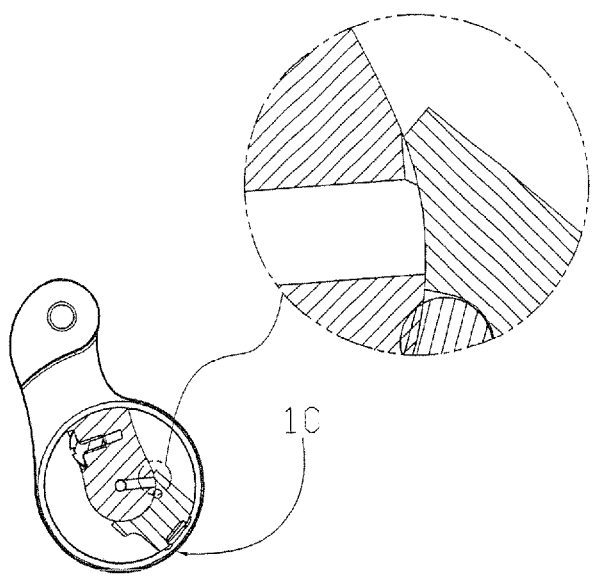
FIG. 18 is a cross sectional view of the hydraulic buffer joint assembly of the present invention.
Figure 18A:
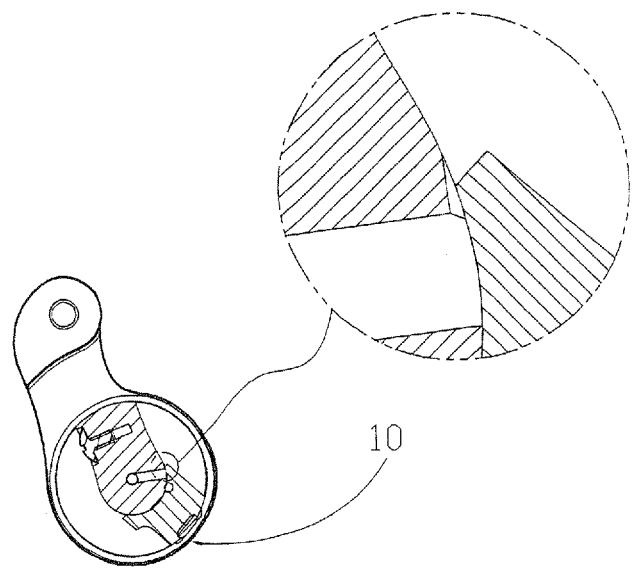
FIG. 18A is another cross sectional view of the hydraulic buffer joint assembly of the present invention.
Figure 19:
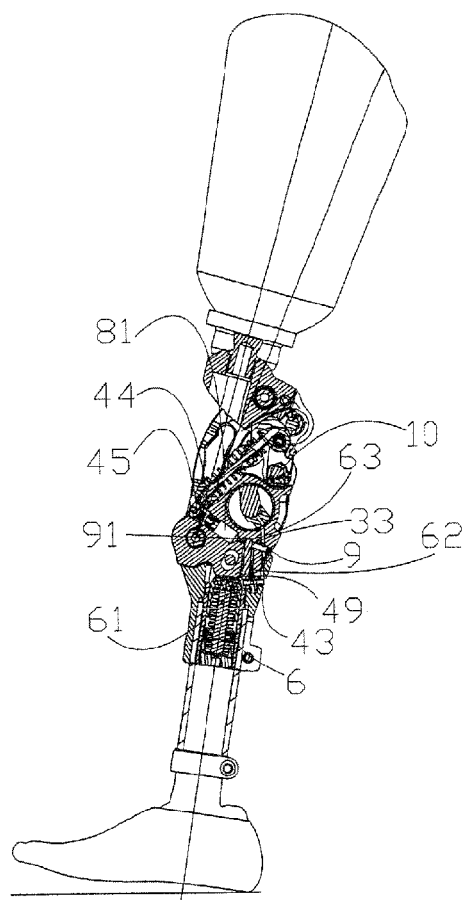
FIG. 19 is an illustration showing the hydraulic buffer joint assembly of the present invention.
Figure 19A:
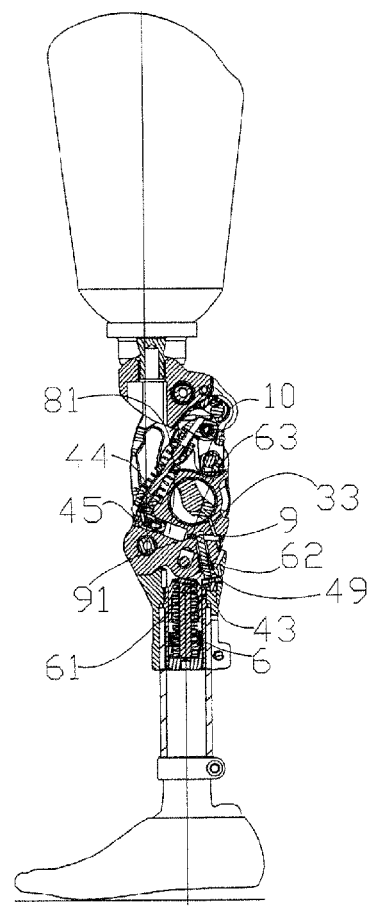
FIG. 19A is another illustration showing the hydraulic buffer joint assembly of the present invention.

As shown in FIGS. 1~19A, the present invention is related to a hydraulic buffer joint assembly, and said hydraulic buffer joint assembly comprises a four-link hydraulic head 1, a motion linkage device 2, a spring device 3, a buffering device 4 and a cushion member 5.

Referring to FIGS. 1~19A again and as shown in the figures, a connecting rod 21 is attached to an inner groove of said four-link hydraulic head 1, and a plurality of perforations 12 provided on an outer side of said four-link hydraulic head 1 are connected with arched slats 28 and pulling rods 22, wherein the arched slats 28 are secured with a needle bearing 24 and a center axle 25 while the pulling rod 22 is secured with a flat-head inner hexagon screw 23 and a center axle 25. A through-hole provided at a lower end of said connecting rod 21 is aligned with said groove of said four-link hydraulic head 1 and is secured thereon by attaching a needle bearing 24 and a center axle 34 thereto. A through-hole provided at a lower end of said pulling rod 22 is aligned with a central hole of a four-link hydraulic body portion 46 and is secured thereon via a flat-head inner hexagon screw 23 fastened thereto. A through-hole provided at a lower end of said four-link hydraulic body portion 46 is aligned with a through-hole of said cushion member 5 and is secured thereon by attaching a needle bearing 24 with a center axle 34 thereto. An outer side of said through-hole of said cushion member 5 is engaged with said arched slats 28 secured thereon via a flat-head inner hexagon screw 23 fastened thereto. An inner groove of said connecting rod 21 is aligned with a through-hole provided on an upper end of said spring device 3 and is secured thereon by attaching a needle bearing 26 and a washer with a center axle 34 thereto. A lower end of said spring device 3 is engaged with a recess 54 of a protrusion 55 extending outward from said four-link hydraulic body portion 46 and is secured thereon by attaching a center 34, a washer 35 and a needle bearing 26 thereto. A lower end of said four-link hydraulic body portion 46 is engaged with a shock absorber 51 attached to a cushion wing 53.

As shown in FIGS. 1~19A, the four-link hydraulic buffer knee joint assembly mainly utilizes the hydraulic center axle 41 to change settings thereof and utilizes a blocker 48 as well as the semi-circular hexagon screw 481 with a one-way ball valve to form an auto-oil-cycling hydraulic mechanism 10. During the operation of the four-link hydraulic buffer knee joint assembly of the present invention, the hydraulic center axle 41 is able to utilize the abovementioned auto-oil-cycling hydraulic mechanism 10 to regulate the hydraulic oil pressure. The one-way ball valve 47 can be used as a one-way valve to control the flow changes during bending and stretching of the joint assembly. The one-way oil filling control mechanism 8 is formed by or constructed from the one-way ball valve 47, spring 33 and loop screw 42. As the hydraulic center axle 41 is turned during the bending of the joint assembly of the present invention, the one-way ball valve 47 is being pushed by the oil pressure thereof to block the entrance such that no further pressure enters into the oil-filling chamber 81. During the stretching of the joint assembly of the present invention, an oil-filling piston 44 is being driven toward an internal of the oil-filling chamber 81 due to the compression force exerted by the spring 33 such that the oil pressure therein can be maintained at a predetermined level. When the lubricant oil in the internal of the oil-filling chamber 81 is reduced to an insufficient amount due to frequent usages of the joint assembly of the present invention, users can detach the adjustable screw 45 from the oil-filling chamber 81 to refill the lubricant oil. An outer side of the hydraulic center axle 41 can be fastened with a star-shaped ring 49, steel balls 491, washers 27 and loop screws 42 to form a fixation screw 43 for securement. The adjustable knobs 411 can too be used for adjusting the speed of the joint assembly of the present invention such that it is of the function of an adjustable buffering speed.

As shown in FIGS. 13~19A, the four-link hydraulic buffer knee joint assembly of the four-link hydraulic main body 46 can be of a changed setting to additionally comprise a controlling axle 6 and wherein said controlling axle 6 comprises a fixation screw 43 penetrating through a star-shaped ring 49, a washer 62, a locking ring 61 and a spring 33. As the oil-filling chamber 81 drives the oil-filling piston 44 to the internal thereof due to the pressing force of the spring 33, the end of the oil passage 9 is maintained with adequate fluid flows along with a stabilized oil pressure by the rolling balls 63. Therefore, during the interchanging of the states of the joint assembly of the present invention from a standing position to a tilted position, the controlling axle 6 provided at the internal of the safety device 7 would not move upward to block the oil passage entrance 91 during the standing position; whereas the controlling axle 6 of the safety device 7 would be driven to move upward to block the oil passage entrance 91 at the top end of the oil passage 9 during the tilted position in order to achieve the blocking of the oil flowing toward the oil passage 9 and such that the buffered safety brake against the ground can be achieved. Nevertheless, it can be understood that the aforementioned embodiments of the present invention are provided for illustrative purposes only and shall not be treated as limitations of the scope of the present invention. In addition, any modifications or changes to the claims or scope of the present invention shall be considered as equivalence of the embodiments of the present invention and are within the scope of the present invention.

is provided at said central hole of said four-link hydraulic head, comprising an oil-filling piston and utilizing a compression spring force, such that an internal auto-filling of oil to a predetermined amount is achieved.

What is claimed is:

1. A hydraulic buffer joint assembly, comprising:
a four-link hydraulic head, a motion linkage device, a spring device, a buffering device and a cushion member assembled with center axles respectively; wherein said four-link hydraulic head is configured to be attached upward to a thigh and a lower end of said cushion member is configured to be attached downward to a calf; and wherein: a connecting rod is attached to an inner groove of said four-link hydraulic head; a plurality of perforations provided on an outer side of said four-link hydraulic head are connected with an arched slat and a pulling rod wherein the arched slats are secured with a needle bearing and a center axle while the pulling rod is secured with a flat head inner hexagon screw and a center axle; a through-hole provided at a lower end of said connecting rod is aligned with said groove of said four-link hydraulic head and is secured thereon by attaching a needle bearing and a center axle thereto; a through-hole provided at a lower end of said pulling rod is aligned with a central hole of a four-link hydraulic body portion and is secured thereon via a flat-head inner hexagon screw fastened thereto; a through-hole provided at a lower end of said four-link hydraulic body portion is aligned with a through-hole of said cushion member and is secured thereon by attaching a needle bearing with a center axle thereto; an outer side of said through-hole of said cushion member is engaged with said arched slats secured thereon via a flat-head inner hexagon screw fastened thereto; an inner groove of said connecting rod is aligned with a through-hole provided on an upper end of said spring device and is secured thereon by attaching a needle bearing and a washer with a center axles thereto; a lower end of said spring device is engaged with a recess of a protrusion extending outward from said four-link hydraulic body portion and is secured thereon by attaching a center axle, a washer and a needle bearing thereto; a lower end of said four-link hydraulic body portion is engaged with a shock absorber attached to a cushion wing; and characterized in that: a hydraulic center axle is provided at said central hole of said four-link hydraulic body portion, comprising an oil-filling piston and utilizing a compression spring force, such that an internal auto-filling of oil to a predetermined amount is achieved.

2. The hydraulic buffer joint assembly according to claim 1, wherein said hydraulic center axle further comprises adjustment knobs provided on two sides of said axle for adjusting a bending speed and a spring-back recovery speed.

3. The hydraulic buffer joint assembly according to claim 1, wherein a changed setting of said four-link hydraulic main body further comprises a controlling axle; and wherein said controlling axle comprises a fixation screw penetrating through a star-shaped ring, a washer, a locking ring and a spring.

4. The hydraulic buffer joint assembly according to claim 3, wherein a changed setting of said four-link hydraulic body portion provided at an internal of said buffering device includes said controlling axle configured to be able to move upward to block an oil passage in order to perform a buffered safety brake against the ground when said controlling axle is subject to a rear tilting downward push.

5. The hydraulic buffer joint assembly according to claim 3, wherein a changed setting of said four-link hydraulic body portion provided at an internal of said buffering device includes said controlling axle having an elevation height adjustable via said fixation screw.

\* \* \* \* \*